United States Patent
Margolis

(12) 
(10) Patent No.: US 6,494,846 B1
(45) Date of Patent: Dec. 17, 2002

(54) DUAL-MODE CATHETER

(75) Inventor: Wayne S. Margolis, Nederland, TX (US)

(73) Assignee: Wayne Margolis Family Partnership, Ltd., Nederland, TX (US)

(*) Notice: Subject to any disclaimer, the term of this patent is extended or adjusted under 35 U.S.C. 154(b) by 12 days.

(21) Appl. No.: 09/597,506

(22) Filed: Jun. 20, 2000

(51) Int. Cl.$^7$ .................................................. A61B 5/00
(52) U.S. Cl. ........................................ 600/585; 604/523
(58) Field of Search ................................. 600/433, 434, 600/435, 595; 604/523–528

(56) References Cited

U.S. PATENT DOCUMENTS

| | | | | |
|---|---|---|---|---|
| 5,389,087 A | * | 2/1995 | Miraki ........................ 604/247 |
| 5,507,774 A | | 4/1996 | Tay et al. ..................... 606/50 |
| 5,571,089 A | | 11/1996 | Crocker ....................... 604/102 |
| 5,776,111 A | | 7/1998 | Tesio ........................... 604/264 |
| 5,810,810 A | | 9/1998 | Tay et al. ..................... 606/50 |
| 5,817,053 A | | 10/1998 | Agarwal ....................... 604/53 |
| 5,921,958 A | * | 7/1999 | Ressemann et al. ......... 604/523 |
| 5,951,568 A | | 9/1999 | Schatz ........................ 606/108 |
| 5,976,106 A | | 11/1999 | Verin et al. ................... 604/96 |

* cited by examiner

*Primary Examiner*—Kevin Shaver
*Assistant Examiner*—Pamela Wingood
(74) *Attorney, Agent, or Firm*—The Matthews Firm

(57) ABSTRACT

The dual mode catheter of the present invention combines an over-the-wire catheter with a MONORAIL (trademark) catheter to allow simultaneous use of and switching between the MONORAIL (trademark) and over-the-wire catheters in situ, for example to manipulate stents, balloons, other medical devices, or combinations thereof. Thus combined, the present invention allows greater control of the medical devices and the catheter by a single physician while simultaneously allowing distal injection of individual components such as iodinated contrast fluids or drugs. Other advantages will be apparent to those of ordinary skill in the medical arts such as reducing necessary exposure to radiation for both doctor and patient.

19 Claims, 3 Drawing Sheets

DUAL-MODE CATHETER

TECHNICAL FIELD

The present invention pertains generally to medical equipment and, more particularly, to a dual mode catheter system and method for using same appropriate for use in percutaneous coronary intervention. The present invention pertains more specifically still to a dual mode catheter combining the abilities of an over-the-wire catheter with the abilities of a MONORAIL (trademark) catheter for use in percutaneous coronary intervention whereby a dual-lumen catheter can be used for delivery of drugs, contrast fluids, and other desired elements through a lumen adapted to further be used for over-the-wire use while simultaneously having a second lumen adapted for use by a shorter wire.

BACKGROUND ART

Percutaneous transluminal coronary angioplasty (PTCA) is a procedure which is well established for the treatment of blockages in the coronary arteries. For example, blockages may occur from cholesterol precipitation on the coronary wall which may be in any stage from initial deposit through aged lesions. PTCA is a technique performed through the skin (percutaneous) inside an artery (transluminal) of the heart (coronary), for example to reshape (angioplasty) that artery. Percutaneous transluminal angioplasty (PTA) is also a known treatment of other types of blocked body lumens.

In general, catheters are used to advance a medical device, such as a balloon or stent, or medical fluid, such as a drug or a contrast fluid, into an artery of a patient to accomplish a desired task inside the artery. For example, in many of today's surgical procedures, medical devices such as catheter mounted angioplasty balloons, incisors, stents and artherectomy cutters are routinely introduced into patients' cardiovascular systems in accordance with prescribed protocols.

One commonly used apparatus for introducing these medical devices is a guide wire. Typically, whenever a guide wire is used for the purpose of introducing a medical device into the cardiovascular system of a patient, the guide wire is pre-positioned in situ, usually through an introducer catheter which is used to establish an access site into the patient's cardiovascular system. In a typical operation, the guide wire is positioned within an artery or other vessel. As the catheter is advanced over the guide wire, a proximal end of the guide wire will remain outside or emerge from a side wall aperture such that the proximal portion of the guide wire remains outside of the catheter as the catheter is advanced to its desired operative site. If it becomes necessary or desirable to exchange a device such as with a balloon dilation catheter, the proximally exposed portion of the guide wire can be secured and stabilized manually by an operator while the first catheter is removed and a second catheter is slid over guide wire.

The most widely used form of percutaneous angioplasty makes use of a dilatation balloon catheter. In typical PTCA or PTA procedures, the cardiovascular system of a patient is accessed with an introducer, usually via the femoral artery, brachial artery, or radial artery. All other devices including a guiding catheter are percutaneously introduced into the cardiovascular system of a patient through the introducer and advanced through a vessel until the distal end thereof is at a desired location in the vasculature. A guide wire and a medical device are introduced through the guiding catheter with the guide wire sliding through the dilatation catheter. The guide wire is first advanced out of the guiding catheter into the patient's coronary vasculature and the requisite device such as a dilatation catheter is advanced over the previously advanced guide wire until the device is properly positioned and the desired procedure is then performed.

At present, two general types of catheters are utilized in clinical practice such as in percutaneous coronary intervention: so-called "over-the-wire" catheters using full length guide wires and "monorail" catheters using shorter guide wires than the over-the-wire catheters. MONORAIL is a trademark of SciMed Life Systems, Inc., One SciMed Place, Maple Grove, Minn., United States of America 55311. Each of these catheter systems has advantages as well as disadvantages. The dual mode catheter of the present invention combines an over-the-wire catheter with a monorail catheter to allow simultaneous use of and switching between the MONORAIL (trademark) and over-the-wire catheters in situ, for example to manipulate stents, balloons, other medical devices, or combinations thereof.

A wide variety of catheters have been developed in the prior art. For example, U.S. Pat. No. 5,776,111 issued to Tesio teaches a multiple catheter assembly having two single catheters each having multiple lumen. Tesio '111 also discusses other typical examples of a multiple lumen catheters such as a dual lumen catheter, commonly known as Tesio catheters, in which one lumen in the catheter tube introduces fluids and the other lumen in the tube removes fluids. Tesio '111 does not teach or suggest having over-the-wire and MONORAIL (trademark) capabilities simultaneously present in a single catheter. In the prior art, such a delivery tube is incapable of supporting a guide wire.

The present invention allows greater control of the medical devices and the catheter by a single physician while simultaneously allowing distal injection of individual components such as iodinated contrast fluids or drugs. Other advantages will be apparent to those of ordinary skill in the medical arts such as reducing necessary exposure to radiation for both doctor and patient.

Over-the-wire catheters incorporate a guide wire lumen extending substantially through the entire length of the catheter. The guide wire lumen is typically separate from catheter mounted devices such as balloons, stents, and the like.

After positioning the guide wire, the catheter mounted medical device is then subsequently advanced through a guiding catheter and over the guide wire. During the advancement of the catheter over the wire, however, it is extremely important for the physician to maintain positive control over both the stability of the guide wire and the advancement of the catheter. Further, it is important that the means for controlling the stability of the guide wire and the means for controlling the advancement of the catheter be relatively close to each other and relatively near the introductory access site into the patient.

An over-the-wire catheter may be used with numerous devices such as stents, balloons, and the like, and also allows distal injections of iodinated contrast fluids and drugs. Further, over-the-wire catheter may be advanced, the guide wire exchanged, and/or a wire tip reshaped without losing ground in situ such as within a coronary artery. However, the long guide wire used in over-the-wire catheters can be difficult to steer when attempting to accurately position the stents, balloons, and the like. Further, advancing such medical devices around, through, or across a coronary obstruction is not easily performable by a single operator.

One solution to the control problem for an over-the-wire catheter is to provide a guide wire of sufficient length so that any extracorporeal portion of the guide wire is longer than the catheter that is being introduced over the wire. Typically, over-the-wire systems incorporate a three hundred centimeter length guide wire. This, however, can be cumbersome and may require manipulation of the system at a substantial distance from introductory access site. A solution to this problem has been the use of so-called MONORAIL (trademark) catheters.

In a MONORAIL (trademark) style of angioplasty catheter, a guide wire lumen extends through only a distal portion of the catheter, typically from a distal tip orifice to a proximal aperture formed in the side wall of the catheter body. The MONORAIL (trademark) catheters in use today have a relatively short guide wire deployed near the distal tip of the catheter so that the guide wire can be separated from the catheter. Typically, MONORAIL (trademark) wires are around one-hundred eighty centimeters in length. This arrangement, however, still requires the physician to effectively control both the guide wire and the catheter.

For over-the-wire systems, exchanging a catheter of device, sometimes desired, is difficult and requires greater exposure to fluoroscopy and radiation. Moreover, such exchanges are not readily performable by a single operator.

MONORAIL (trademark) catheters do not provide for distal injection of iodinated contrast fluids or drugs or the like. Wire exchanges and wire tip reshaping are not performable without removing the wire entirely from the body, leading to loss of ground of any initial advancement within the coronary artery. Second lumen within MONORAIL (trademark) catheters may allow for passage of wires such as those to deliver radioactive therapies, but do not extend through the entire length of the catheter and are not adapted to receive and support a guide wire.

Several catheters and techniques for positioning medical devices in the cardiovascular systems of patients have been previously proposed in the prior art. For example, U.S. Pat. No. 5,951,568 to Schatz teaches an over-the-wire catheter including a catheter that is formed with a lumen for receiving a guide wire there through. In operation, the guide wire is pre-positioned as desired and an end of the guide wire is then passed through an orifice of a connector and is inserted into the guide wire lumen of the catheter. The distal end of the catheter is then inserted over the wire and through the orifice of the connector. The catheter is advanced through the orifice of the connector and over the guide wire. No suggestion is made to combine a short wire style catheter with an over-the-wire style.

U.S. Pat. No. 5,976,106 to Verin et al teaches a dual or triple lumen catheter wherein the lumen means may be closed distally. The catheter may comprise a long guide wire lumen with an entry and an exit distal of the balloon, which advantageously results in a two lumen catheter construction. The catheter may also comprise a guide wire lumen with an entry distal of the balloon and an exit proximal of the balloon. However, Verin '106 teaches that the long guide wire lumen is closed at one end and that the purpose of such a long guide wire lumen is not for use as an over-the-wire catheter guide or fluid delivery but rather as a means to allow entry of a radioactive emitter, which makes limiting travel within the long guide wire lumen necessary for safety purposes. No teaching or suggestion exists to combine over-the-wire and MONORAIL (trademark) for simultaneous use. Verin '106 also teaches a balloon at the distal functional end.

U.S. Pat. No. 5,817,053 to Agarwal teaches a guide catheter exchange device for exchanging a guide catheter advanced over a balloon catheter and a coronary guide wire without removing the coronary guide wire in percutaneous transluminal coronary angioplasty. In one embodiment, the exchange device comprises two sections and a connecting device for connecting the sections. In a separate embodiment, the invention pertains to a guide catheter exchange device for exchanging a guide catheter employed by a MONORAIL (trademark) balloon catheter.

As noted in Agrawal '053, a report in Catherization and Cardiovascular Diagnosis 33, pp. 284–287 (1994) describes a catheter reported to contain two inner lumen and four ports providing a partial MONORAIL (trademark) design wherein the exchange technique requires a moderate amount of operator skill and a learning curve. The exchange of the guide catheter requires threading the coronary guide wire through an exit port of the exchange device located 120 cm proximal to the distal tip of the device and reinserting the coronary guide wire through a re-entry port of the exchange device located 130 cm proximal to the distal tip of the device.

U.S. Pat. No. 5,571,089 issued to Crocker teaches a low profile perfusion catheter for use in coronary angioplasty applications. In one embodiment, an axially movable tubular support is movable within a lumen from a proximal, insertion position to a distal perfusion position. In a further embodiment, a porous drug delivery balloon is provided. Crocker '089 teaches away from a dual mode catheter.

Accordingly, the prior art, although discussing possible use of either over-the-wire or MONORAIL (trademark) catheters, discusses these as mutually exclusive alternatives. No suggestion is made to combine an over-the-wire catheter with a MONORAIL (trademark) catheter. No suggestion is made to provide a second guide wire lumen capable of supporting a manipulatable guide wire there through in addition to allowing use such as for fluid or drug delivery.

Moreover, disadvantages still remain. None of the prior art catheters teach simultaneous provision of or switching between a MONORAIL (trademark) and an over-the-wire catheter in situ, for example to manipulate stents, balloons, other devices, or combinations thereof. No prior art exists that teaches how to allow distal injection of individual components such as iodinated contrast fluids or drugs while simultaneously allowing a MONORAIL (trademark) catheter to be in place.

Accordingly, an improved dual mode catheter is described.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

GENERAL DESCRIPTION AND PREFERRED MODE FOR CARRYING OUT THE INVENTION

Figure 1:
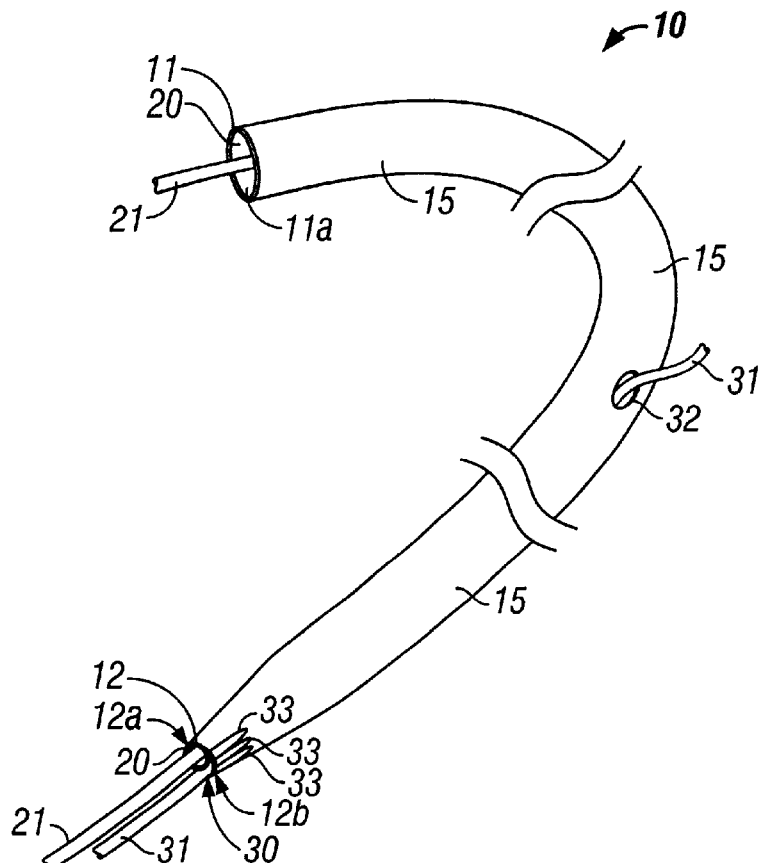
FIG. 1 is a partial fragmentary perspective view of an embodiment of the dual mode catheter of the current invention.

Referring now to FIG. 1, the present invention's dual mode catheter, herein generally referred to by the numeral "10," generally comprises first lumen 20 and second lumen 30 disposed within elongated tubular body 15.

As is well known in the art, dual mode catheter 10 generally comprises elongate tubular body 15 extending between proximal control end 11 and distal functional end 12. Elongate tubular body 15 ranges in length from around eighty cm to around two hundred and fifty centimeters with the actual desired length of tubular body 15 depending upon the desired application. For example, lengths in the area of about one hundred centimeters to about one hundred eighty centimeters are typical for use in percutaneous transluminal angioplasty applications. Tubular body 15 may be produced in accordance with any of a variety of known techniques for manufacturing catheter bodies, such as by extrusion of appropriate biocompatible plastic materials or by other techniques all of which are well understood in the catheter art.

In the preferred embodiment, distal functional end 12 is insertable into a desired target such as a human being. Each end of dual mode catheter 10—distal functional end 12 and proximal control end 11—may additionally have one or more orifices, as in the currently preferred embodiment, such as distal functional end orifices 12a and 12b and proximal control end orifice 11a, that are in communication with one or more lumen such as 20 or 30 to accept one or more guide wires or medical devices, allow passage of fluids or liquids, or any combination thereof.

Tubular body 15, in accordance with the present invention, is provided with a generally circular cross-sectional configuration. Alternatively, other non-circular cross-sections may be used such as by way of example and not limitation oval or triangular cross-sections, depending upon the method of manufacture and the intended use. As is well known in the art, interior diameters and other dimensions such as exterior diameters and/or peripheries will be dependant on the intended purpose of dual mode catheter 10, by way of example and not limitation such as a function of the number of fluid, liquid, or other functional lumen contained in dual mode catheter 10, together with the acceptable maximum flow rate of dilatation fluid or drugs to be delivered through dual mode catheter 10 and the desired structural integrity.

Tubular body 15 must have sufficient structural integrity to permit dual mode catheter 10 to be advanced into arterial or other desired locations without buckling or undesirable bending of tubular body 15. In addition, tubular body 15 must have sufficient integrity at distal functional end 12 to accept two separate, manipulable guide wires, first guide wire 21 and second guide wire 31. At the same time, tubular body 15 must present a low profile for advancement within the vessel into which dual mode catheter 10 has been inserted.

First lumen 20 is adapted to receive desired drugs or other desired fluid or liquid material there through. First lumen 20 is further adapted to receive and support manipulation of first guide wire 21. Proximal control end orifice 11a, located near proximal control end 11, and distal functional end orifice 12a, located near distal functional end 12, are also adapted to receive first guide wire 21 there through. The diameter of either the long guide wire or the short guide wire can range from between 0.005 and 0.025 inches with a typical diameter of around 0.014 inches in diameter. In the presently preferred embodiment, first guide wire 21 is approximately 0.014 inches in diameter and first lumen 20 adapted to support such a guide wire. In the prior art, a MONORAIL (trademark) catheter may have a lumen such as first lumen 20 extending from distal functional end 12 through to proximal control end 11, but such a lumen is not able to support insertion and manipulation of a guide wire such as first guide wire 21.

First guide wire 21 normally exits through first lumen 20 at proximal control end 11 through proximal control end orifice 11a. First guide wire 21 has a predetermined length which is at least as long as the length of dual mode catheter 10 along elongate tubular body 15. In the preferred embodiment, this length is greater than the length of dual mode catheter 10 from distal functional end 12 to proximal control end 11 and can range from around one hundred centimeters to around four hundred centimeters with a typical length of around three hundred centimeters.

Figure 2A:
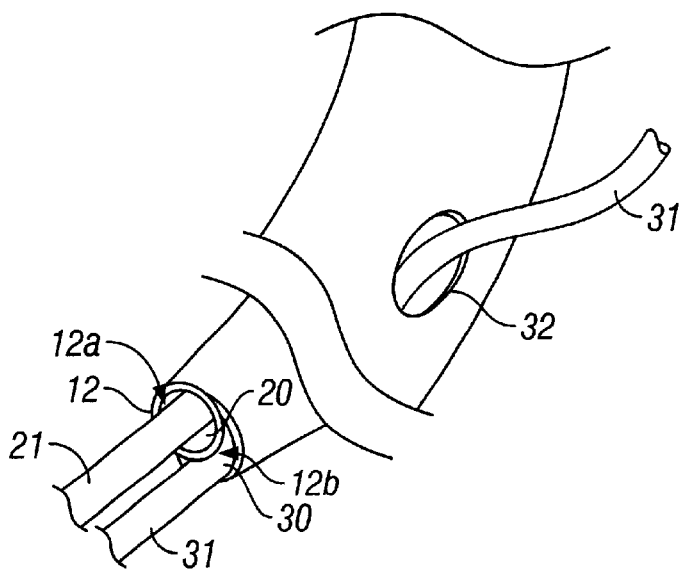
FIG. 2a is a partial fragmentary perspective view of the tip end of an embodiment of the dual mode catheter of the current invention.
Figure 2B:
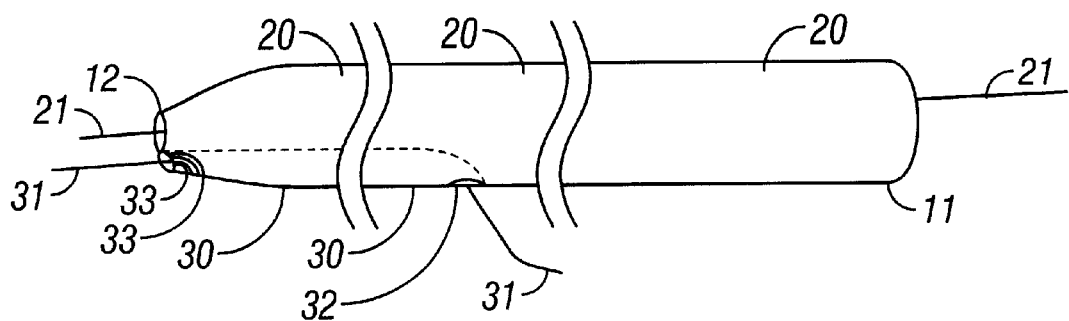
FIG. 2b is an elevated view (as viewed at a slight angle from the side) of a distal functional end of the current invention showing two internal lumen.
Figure 2C:
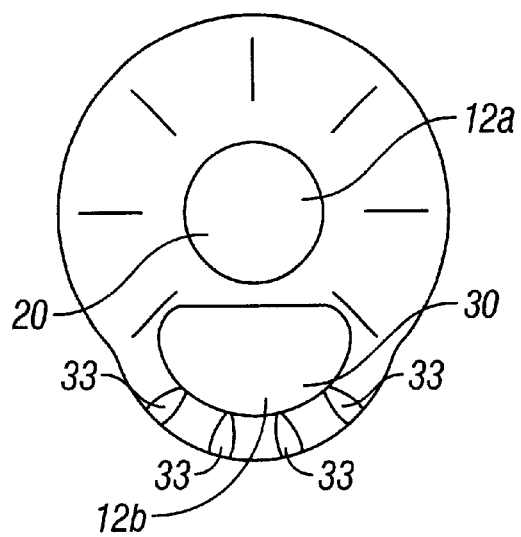
FIG. 2c is a plan view of the tip end of an embodiment of the current invention.

Referring now to FIG. 2a through FIG. 2c, additionally, in the preferred embodiment dual mode catheter 10 further comprises second lumen 30. Distal functional end orifice 12b, located near distal functional end 12, and aperture 32 are adapted to receive second guide wire 31 there through. In the preferred embodiment, aperture 32 allows second lumen 30 to be in communication with an outer surface of tubular body 15, allowing second guide wire 31 to pass through aperture 32 into second lumen 30 and out through distal functional end orifice 12b located near distal functional end 12.

Distal functional end 12 may be of any shape appropriate for insertion into and guidance through an intended vessel such as an artery. In the presently preferred embodiment, distal functional end 12 is generally tapered such as in a substantially conical configuration with provision to have distal functional end orifices 12a and 12b present to allow passage of short guide wire 31 and long guide wire 21 there through. Additionally, as in the preferred embodiment, distal functional end 12 is further adapted to safely cross through lesions in the vessel into which dual mode catheter 10 is inserted.

In the prior art, MONORAIL (trademark) style catheters are adapted to accept and be joined onto balloons or other such devices at distal functional end 12. Dual mode catheter 10 is not adapted to accept and be joined onto balloons or other such devices at distal functional end 12 but is intended to be used to deliver fluids such as contrast fluids or drugs or the like to a distal position through distal functional end 12.

In a presently preferred embodiment, distal functional end orifice 12b is further distinguished either visually, tactily, through an addition differentiator such as radiographically, or any combination thereof. By way of example and not limitation, distal functional end orifice 12b may be a different color than the rest of dual mode catheter 10 to visually clue a manipulator that aperture 32 is the aperture designated to receive second guide wire 31 there through. In similar manner, distal functional end orifice 12b may have a different shape, have bumps or ridges or indentations or the like such as shown at 33 or other tactile differentiations, or any combination thereof.

Referring now to FIG. 2*b*, second lumen 30 is isolated from first lumen 20 within dual mode catheter 10 and extends from distal functional end 12 a predetermined length towards proximal control end 11. As shown in this example, second lumen 30 may be in communication with aperture 32 which, in turn, is in communication with an outer circumference of tubular body 15.

Figure 2D:
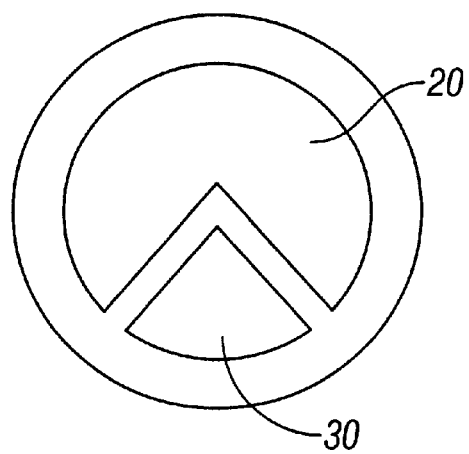
FIG. 2d is a plan view of the tip end of an alternative embodiment of the current invention.

Referring now to FIG. 2*c* and FIG. 2*d*, distal functional end orifice 12*b* may be further visually differentiated from distal functional end orifice 12*a* such as by shape, radiographic opacity, color, or any combination thereof and may have differing internal configurations such as shown in FIG. 2*c* and FIG. 2*d*.

Referring now to FIG. 2*c* and FIG. 2*d*, numerous internal configurations of first lumen 20 and second lumen 30 are anticipated by the present invention, as required by a specific use of and delivery anticipated for dual mode catheter 10. By way of example and not limitation, first lumen 20 and second lumen 30 may be internal passageways of tubular body 15 as shown in FIG. 2*d*. In an alternative current anticipated, each lumen 20 and 30 may be co-equal or, as shown in FIG. 2*c*, one lumen may be larger than the other in order to accommodate a desired function such as delivery of contrast fluid or drugs.

Figure 3A:
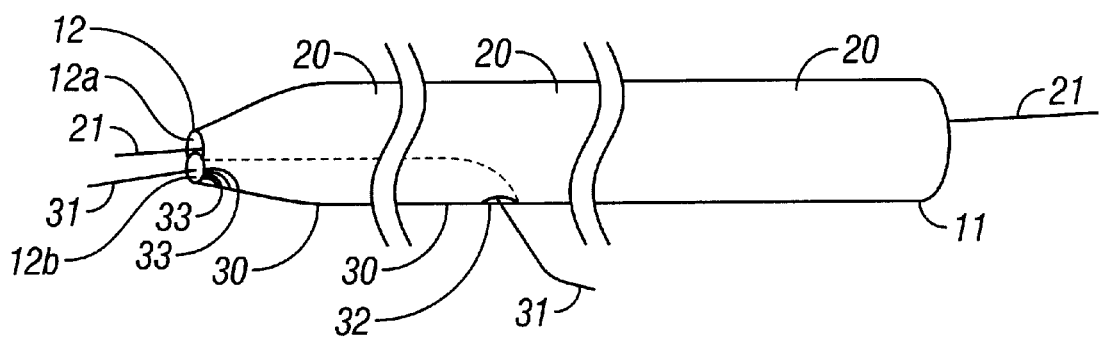
FIG. 3a is an elevated view (as viewed at a slight angle from the side) of a portion of an embodiment of the current invention showing a tapered tip.
Figure 3B:
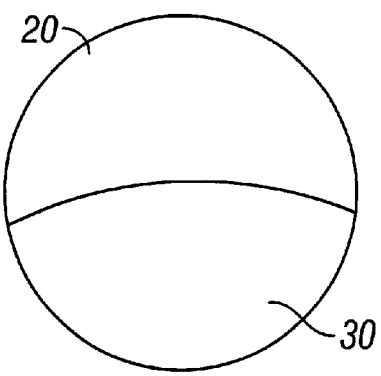
FIG. 3b is a front plan view of an end of the current invention showing an alternate arrangement of two internal lumen.

Referring now to FIG. 3*a*, aperture 32, second lumen 30, and distal functional end orifice 12*b* are adapted to receive second guide wire 31 which will then exit second lumen 30 at distal functional end orifice 12*b*, such as by way of example and not limitation through distal functional end orifice 12*a*. Second guide wire 31 has a predetermined length which, in the preferred embodiment, is less than the length of first guide wire 21. In the preferred embodiment, second guide wire 31 can range from around fifty centimeters to around two hundred and fifty centimeters with a typical length of around one hundred eighty centimeters in length. The diameter of either the long guide wire or the short guide wire can range from between 0.005 and 0.025 inches with a typical diameter of around 0.014 inches in diameter.

Figure 4:
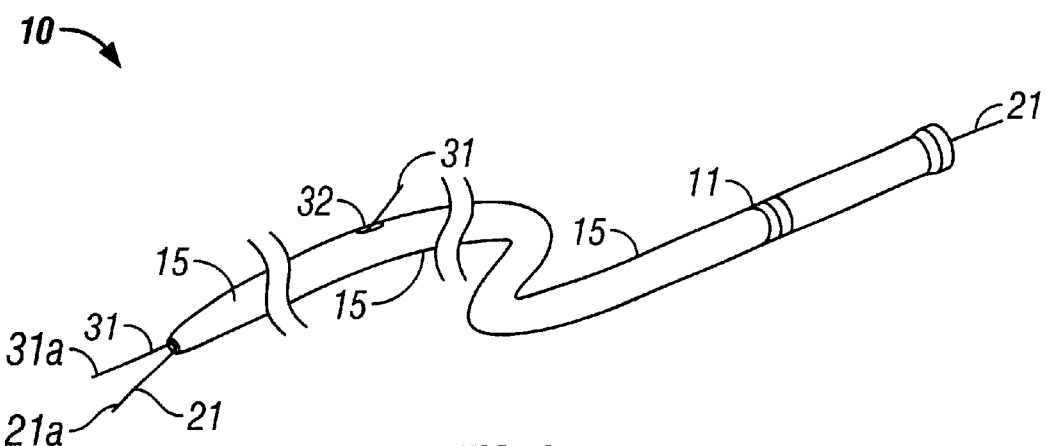
FIG. 4 is a partial fragmentary perspective view of a dual mode catheter.

In the operation of the preferred embodiment, referring now to FIG. 4, two examples are given of use of dual mode catheter 10. These examples are not intended to be a limitation with respect to the features of the invention as claimed, and these and other objects can be more readily observed and understood in the detailed description of the preferred embodiment above and in the claims.

In a first example, a guide catheter is first placed in an right coronary artery (RCA) osteum (not shown in the figures). A complex mid-RCA stenosis is then wired with a coronary guide wire (not shown in the figures), typically one hundred eighty centimeters in length, as will be familiar to those of ordinary skill in the surgical arts. A tip of the coronary guide wire is placed distal to the stenosis, and a MONORAIL (trademark) balloon (not shown in the figures) advanced to a predetermined location, inflated, and then deflated. The MONORAIL (trademark) balloon is then removed over the coronary guide wire, leaving the coronary guide wire in the distal RCA.

Dual mode catheter 10 is placed over the coronary guide wire with an end of the coronary guide wire inserted through second lumen 30. Dual mode catheter 10 is then advanced into the distal RCA over the coronary guide wire.

At this juncture, other procedures may be performed. By way further example, contrast fluid may be injected through first lumen 20, the over-the-wire lumen. If contrast injection reveals a thrombus at the dilation site, mechanical thrombectomy may be indicated and an angiojet device, which requires a long guide wire, selected. In this case, dual mode catheter 10 is advanced over short guide wire 31 through second lumen 30 into the distal RCA. Long guide wire 21 is then advanced through first lumen with wire tip 21*a* distal to end 12. Dual mode catheter 10 and short guide wire 31 are removed over long guide wire 21, and the desired device, in this example an angiojet (not shown in the figures), is advanced over long guide wire 21. Normal procedures as known to those in the medical arts are then performed as in the prior art.

In a further example, a guide catheter (not shown in the figures) is placed in a left main artery. Short guide wire 31 is advanced across a severe stenosis in a proximal LAD. Intra-coronary ultrasound is performed, revealing napkin ring calcification of the LAD stenosis. A decision is made to perform rotabladder atherectomy.

Dual mode catheter 10 is then passed into the LAD over short guide wire 31 and positioned distally to a predetermined position in situ. A specialized rotabladder guide wire is then inserted via first lumen 20 into the distal LAD. Short guide wire 31 and dual mode catheter 10 are then removed over the rotabladder guide wire allowing the rotational atherectomy to be performed. Following the atherectomy, short guide wire 31 is reinserted into second lumen 30 without any guide wire protruding from distal functional end 12. A proximal control end of short guide wire 31 is secured into a guide wire holder at proximal control end 11 and dual mode catheter 10 advanced over the rotabladder guide wire via first lumen 20. Short guide wire 31 is then advanced distal to dual mode catheter 10. Dual mode catheter 10 and the rotabladder guide wire are then removed over short guide wire 31. A stent (not shown in the figures) may then be advanced over short guide wire 31 and deployed.

It may be seen from the preceding description that an improved dual mode catheter has been provided.

It is noted that the embodiment of the improved dual mode catheter described herein in detail for exemplary purposes is of course subject to many different variations in structure, design, application and methodology. Because many varying and different embodiments may be made within the scope of the inventive concepts herein taught, and because many modifications may be made in the embodiment herein detailed in accordance with the descriptive requirements of the law, it is to be understood that the details herein are to be interpreted as illustrative and not in a limiting sense.

What is claimed is:

1. An improved non-balloon dual mode catheter capable of simultaneous insertion over at least one long guide wire and at least one short guide wire, the long guide wire longer than the short guide wire, the catheter comprising:

a substantially tubular member having a proximal control end and a distal functional end;

a long guide wire lumen disposed within the tubular member, the long guide wire lumen being substantially coextensive with the tubular member and further comprising a first exit aperture located proximate the proximal control end and a second exit aperture located proximate the distal functional end; the long guide wire lumen adapted to receive a long guide wire therethrough and further adapted to receive fluids therethrough; the long guide wire being moveable with respect to the long guide wire lumen during use;

a short guide wire lumen disposed within the tubular member, the short guide wire lumen adapted to receive a short guide wire therethrough, the short guide wire lumen further comprising an exit aperture disposed proximate the distal functional end; and a short guide wire aperture, adapted to receive a short guide wire, the short guide wire aperture disposed through an outer surface of the tubular member and located intermediate the proximal control end and the distal functional end, the short guide wire aperture in communication with the short guide wire lumen whereby the short guide wire lumen is in communication with the outer surface of the tubular member through the short guide wire aperture.

2. The improved dual mode catheter of claim 1 wherein a long guide wire is inserted into the long guide wire lumen, the long guide wire is longer than the tubular member.

3. The improved dual mode catheter of claim 1 wherein a long guide wire or a short guide wire inserted into the long guide wire lumen or the short guide wire lumen respectively has a diameter of between 0.005 and 0.025 inches.

4. The improved dual mode catheter of claim 1 wherein the tubular member has a length of approximately 100 cm to 200 cm.

5. The improved dual mode catheter of claim 1 wherein the tubular member has a length of approximately 150 cm to 200 cm.

6. The improved dual mode catheter of claim 1 wherein the tubular member has a length of approximately 150 cm to 400 cm.

7. The improved dual mode catheter of claim 1 wherein the long guide wire has a length of between around 150 cm to around 400 cm.

8. The improved dual mode catheter of claim 1 wherein the short guide wire lumen exit aperture is tactily distinguishable from the long guide wire exit aperture at the distal functional end.

9. The improved dual mode catheter of claim 1 wherein the short guide wire lumen exit aperture is visually distinguishable from the long guide wire exit aperture at the distal functional end.

10. An improved method of using a non-balloon dual mode catheter, the dual mode catheter comprising a substantially tubular member having a length of approximately 100 cm to 300 cm having a proximal control end and a distal functional end; a long guide wire having a length of approximately 150 cm to 400 cm in length; a short guide wire having a length of approximately 150 cm to 250 cm in length; a long guide wire lumen disposed internal to the tubular member and substantially coextensive in length with the tubular member, the long guide wire lumen having a distal aperture at the distal functional end of the tubular member and a proximal aperture at the proximal control end of the tubular member; and a short guide wire lumen disposed internal to the tubular member, the short guide wire lumen having a distal aperture proximate the distal functional end of the tubular and a short guide wire aperture located intermediate the proximal control end and the distal functional end of the tubular; wherein the long guide wire lumen is adapted to receive the long guide wire therethrough; and the short guide wire lumen is adapted to receive the short guide wire therethrough with an end of the short guide wire exiting the dual mode catheter through the short guide wire aperture, the method comprising the steps of:

positioning the short guide wire in situ;

placing the dual mode catheter over the short guide wire with an end of the short guide wire inserted through the second lumen distal aperture into the second lumen and exiting the short guide wire aperture;

advancing the dual mode catheter over the short guide wire;

inserting a long guide wire through the distal aperture of the long guide wire lumen through the long guide wire lumen and out the functional aperture of the long guide wire lumen;

navigating the dual mode catheter and short guide wire to a desired position over the long guide wire; and navigating a desired medical device into place in situ through a guide wire catheter over the long guide wire.

11. The improved dual mode catheter of claim 1 wherein the distal functional end is tapered.

12. An improved method of using a dual mode catheter, the dual mode catheter comprising a substantially tubular member of between around 100 cm to around 300 cm having a proximal control end and a distal functional end; a long guide wire of around 150 cm to around 400 cm in length; a short guide wire of around 150 cm to around 250 cm in length; long guide wire lumen disposed internal to the tubular member and substantially coextensive in length with the tubular member, the long guide wire lumen having an distal aperture at the distal functional end of the tubular member and a proximal aperture at the proximal control end of the tubular member; and a short guide wire lumen disposed internal to the tubular member, the short guide wire lumen having an distal aperture proximate the distal functional end of the tubular and a short guide wire aperture located intermediate the proximal control end and the distal functional end of the tubular; wherein the long guide wire lumen is adapted to receive the long guide wire there through; and the short guide wire lumen is adapted to receive the short guide wire there through with an end of the short guide wire exiting the dual mode catheter through the short guide wire aperture, the method comprising the steps of:

positioning the short guide wire in situ;

placing the dual mode catheter over the short guide wire with an end of the short guide wire inserted through the second lumen distal aperture into the second lumen and exiting the short guide wire aperture;

advancing the dual mode catheter over the short guide wire;

inserting a long guide wire through the distal aperture of the long guide wire lumen through the long guide wire lumen and out the functional aperture of the long guide wire lumen;

navigating the dual mode catheter and short guide wire to a desired position over the long guide wire; and navigating a desired medical device into place in situ through a guide catheter over the long guide wire.

13. The improved method of claim 10 further comprising the step of exchanging a long guide wire for a short guide wire to allow for injection of fluids through the long guide wire lumen.

14. The improved method of claim 12 further comprising the step of exchanging a long guide wire for a short guide wire to allow for injection of fluids through the long guide wire lumen.

15. The improved method of claim 14 wherein the fluid is a drug.

16. The improved method of claim 14 wherein the fluid is a contrast fluid.

17. The improved method of claim 12 further comprising the step of selectively removing either the short guide wire or the long guide wire.

18. The improved method of claim 12 wherein both the short guide wire and the long guide wire are present simultaneously in the catheter.

19. The improved method of claim 12 wherein the medical device is selected from the group of medical devices consisting of catheter mounted angioplasty balloons, incisors, stents, artherectomy cutters, fluids, and angiojets.

* * * * *